(12) United States Patent
Moen et al.

(10) Patent No.: US 9,006,500 B2
(45) Date of Patent: Apr. 14, 2015

(54) HYDRATE INHIBITOR RECOVERY PROCESS

(75) Inventors: Kolbjørn Moen, Oslo (NO); Jon Even Vale, Gjettum (NO); Geir Vingelven, Høvik (NO)

(73) Assignee: Aker Process Systems AS, Lysaker (NO)

( * ) Notice: Subject to any disclaimer, the term of this patent is extended or adjusted under 35 U.S.C. 154(b) by 0 days.

(21) Appl. No.: 14/232,009

(22) PCT Filed: Jul. 18, 2012

(86) PCT No.: PCT/IB2012/053653
§ 371 (c)(1),
(2), (4) Date: Apr. 14, 2014

(87) PCT Pub. No.: WO2013/011462
PCT Pub. Date: Jan. 24, 2013

(65) Prior Publication Data
US 2014/0256990 A1    Sep. 11, 2014

(30) Foreign Application Priority Data
Jul. 20, 2011   (NO) .................................. 20111047

(51) Int. Cl.
| C07C 29/76 | (2006.01) |
| B01D 1/22 | (2006.01) |
| F26B 17/20 | (2006.01) |
| F26B 25/00 | (2006.01) |
| B01D 21/26 | (2006.01) |
| F26B 21/14 | (2006.01) |

(52) U.S. Cl.
CPC ................ C07C 29/76 (2013.01); B01D 1/225 (2013.01); F26B 17/20 (2013.01); B01D 21/262 (2013.01); F26B 21/14 (2013.01); F26B 25/006 (2013.01)

(58) Field of Classification Search
None
See application file for complete search history.

(56) References Cited

U.S. PATENT DOCUMENTS

| 3,678,596 A | 7/1972 | Kubo |
| 3,977,936 A | 8/1976 | Murakami et al. |
| 6,340,373 B1 | 1/2002 | Billington |
| 7,232,505 B2 * | 6/2007 | Laborie et al. .................. 203/18 |
| 2005/0072663 A1 | 4/2005 | Laborie et al. |

FOREIGN PATENT DOCUMENTS

| CH | 680 948 | 12/1992 |
| EP | 0 588 152 | 3/1994 |
| NO | 20056113 | 6/2007 |
| WO | 2007/073204 | 6/2007 |

OTHER PUBLICATIONS

International Search Report issued Feb. 8, 2013 in International Application No. PCT/IB2012/053653.
Norwegian Search Report issued Feb. 17, 2012 in corresponding European patent application No. 20111047.
Written Opinion of the International Searching Authority issued Feb. 8, 2013 in International Application No. PCT/IB2012/053653.

* cited by examiner

*Primary Examiner* — Brian J Davis
(74) *Attorney, Agent, or Firm* — Wenderoth, Lind & Ponack, L.L.P.

(57) ABSTRACT

A system and method for recovery of hydrate inhibitor from a fluid comprising hydrate inhibitor, water, mineral salt ions and salt particles is disclosed. Wherein, the system comprises: —an indirectly heated paddle dryer with a fluid inlet, at least one vapor outlet and a dry salt outlet —a vapor separation unit in fluid communication with the at least one vapor outlet for separation of the vapor to recover the hydrate inhibitor.

14 Claims, 8 Drawing Sheets

HYDRATE INHIBITOR RECOVERY PROCESS

The present invention relates to a method and system for recovery of hydrate inhibitor (HI) especially the present invention relates to the recovery of HI from salt slurries obtained after pretreatment and salt slurries obtained after reclamation.

BACKGROUND

It is well known that well streams containing a mixture of fluids such as crude oil, condensate, formation water and gas during transportation may react and form solid hydrates resulting in i.e. blocked pipelines. To avoid and or limit the formation of hydrates compounds known as hydrate inhibitors are added to the well stream prior to transportation. One example of an often applied hydrate inhibitor is mono-ethylene glycol (MEG), other applicable hydrate inhibitors include glycol compounds with other substituents, as well as kinetic hydrate inhibitors or combinations thereof. The term kinetic refers to the effect of the inhibitor lowering the reaction rate of the hydrate forming reactions.

Hydrate inhibitors such as MEG are valuable chemicals and the recycling thereof provides reduced costs. However equally important are the environmental consequences, as waste streams containing not inconsiderable amounts of MEG or similar inhibitors can not be released to the environment.

A number of different steps and methods for separating MEG for reuse are known in the art.

After a first separation of hydrocarbons the process fluid normally comprises a hydrocarbon rest, water, corrosion products, MEG and dissolved mineral salts. Normally the amount of mineral salts is considerable and the salts may precipitate during the MEG extraction process which again leads to increased viscosity, sludge formation or plugging. Depending on the formation the composition of the mineral salts will vary. It is well known to remove salts from solutions by precipitation of solids by increasing the activity or concentration; however the combination of alkali and earth alkali ions, and halogen, carbonate and bicarbonate ions results in the precipitation of relatively small salt particles that are not easily separated from the solution. A further obstacle for the regeneration process is degradation of the inhibitor at high temperatures which limits the heating possibility to obtain separation.

PRIOR ART

Different technical solutions have been developed to extract inhibitor and handle the salt problem. Examples of these techniques are disclosed in U.S. Pat. No. 6,340,373 and US2005/0072663 and US2010/0191023.

US2010/0191023 discloses a reclamation process adapted to form calcium carbonate particles with increased particle size which can be removed in a filtration unit.

U.S. Pat. No. 6,340,373 discloses a method where a part of the inhibitor and a part of the water is evaporated, and the vapour phase is removed, separated and condensed forming an inhibitor stream applicable for reuse. The rest comprises mainly inhibitor and mineral salts and is fed to a reduction and crystallization unit where a part of the salts are precipitated and removed. The particle separation can be performed in several steps. The obtained particle stream will in addition to salt particles contain a glycol rest and a water rest.

US2005/0072663 describe a process for regeneration of a glycol solution where the solution is expanded, distilled and fed to a regeneration column under vacuum to remove water and precipitate the salts, where after the salts are separated from the glycol. The separation of the salts is performed employing a centrifugal separation device. Thereby a salt stream is obtained, however this salt stream also comprises a glycol rest.

The known methods results in the formation of a slurry comprising salt particles as well as salts dissolved in a mixture of water and hydrate inhibitor. The salt particles are often very small and therefore difficult to separate from the liquid through traditional solids separation equipment. Further the divalent ions such as $Ca^{2+}$ and $Fe^{2+}$ have a tendency to form sticky carbonate salts, which are problematic to handle.

OBJECTIVES OF THE INVENTION

The aim of the present invention is to provide a method and system for separating of hydrate inhibitor from a salt stream obtained through solid separation of precipitated salts. Depending on the employed regeneration process, reclamation system and the separation method the composition of the salt streams will vary.

It is further an objective of the present invention to provide a method and system applicable independently of the employed method of regeneration and/or reclamation of the hydrate inhibitor.

It is also a goal to provide a system applicable to handle both small and potentially sticky salt particles.

A further goal is to provide a continuous system that can be connected to existing continuously running inhibitor regenerating systems.

It is further intended to provide a system and method resulting in solid waste consisting of dried salts which is easy to handle and with a so limited content of hydrate inhibitor that the possibilities of disposal are not negatively influenced thereby.

Further the invention aims at providing a method which can be performed at conditions which do not result in degeneration of the hydrate inhibitor.

Surprisingly the present inventors have now been able to provide a system and a method that allows for recovery of the inhibitor and drying of the salts in a continuously manner without causing degeneration of the inhibitor.

According to a first aspect the present invention provides a system for recovery of hydrate inhibitor from a fluid comprising hydrate inhibitor, water, mineral salt ions and salt particles, wherein the system comprises:
  an indirectly heated paddle dryer with a fluid inlet, at least one vapor outlet and a dry salt outlet
  a vapor separation unit in fluid communication with the at least one vapor outlet for separation of the vapor to recover the hydrate inhibitor.

In one aspect of the present invention the system further comprises at least one centrifuge with a fluid inlet, a liquid outlet and a concentrated fluid outlet, wherein the concentrated fluid outlet is in fluid communication with the fluid inlet of the indirectly heated paddle dryer. In a preferred embodiment the at least one centrifuge is a disk stack type centrifuge or a decanter type centrifuge.

In one embodiment with respect to this aspect of the invention the system may further comprise a salt precipitation unit upstream the at least one centrifuge.

In another aspect of the present invention the heated paddle dryer further comprises an inert gas inlet. Here the inlet gas may be employed as a sweep gas. The system may further comprise an inert gas separation unit in fluid communication with the at least one vapor outlet and comprising an inert gas outlet in fluid communication with the inert gas inlet of the paddle dryer. In this aspect of the invention the system may further comprise a heater upstream the inert gas inlet. In one embodiment of the invention a cross heat exchanger is employed between inert sweep gas flow entering the paddle dryer and the gas stream exiting the paddle dryer, thereby heat is transferred from the existing gas to the gas flow entering the paddle dryer.

In one embodiment of the system the heated paddle dryer may further comprise a downstream unheated or cooled area. Here downstream refers to downstream the fluid inlet.

In another aspect of the invention the system comprises an adjustment agent inlet upstream the process stream inlet to the paddle dryer for adding water and or salts for adjusting the composition of the process stream. The heated paddle dryer may in one embodiment thereof comprise a plurality of vapor outlets arranged in the part of the paddle dryer closest to the dry salt outlet.

According to a second aspect the present invention provides a method for recovering hydrate inhibitor from a fluid comprising water, hydrate inhibitor mineral salt ions and salt particles, wherein the method comprises
  evaporating water and hydrate inhibitor from the fluid with an indirectly heated paddle dryer, thereby obtaining vapor and a dry solid salt residue;
  recovering the hydrate inhibitor from the vapor.

In one aspect of the invention the method further comprises increasing the concentration of salt particles in the fluid by centrifugation prior to the evaporation, whereby a separate liquid stream is obtained. Regarding this aspect of the invention the hydrate inhibitor may in one embodiment thereof be recovered from the separate liquid stream. Further the method may comprise combining the separated liquid with the vapor and recover the hydrate inhibitor from the combined stream.

In another aspect of the present invention the recovering is obtained by a combination of water separation, evaporation and condensation.

In yet another aspect of the present invention the method further comprises sweeping with an inert sweep gas stream over the fluid in the indirectly heated paddle dryer during the evaporation. In one embodiment of the aspect of the present invention the inert sweep gas is separated from the vapor, heated and recycled as sweep gas. In another embodiment the inert sweep gas stream before entering the paddle dryer is heat exchanged with the vapor.

In one aspect of the present invention the method further comprises cooling the dry solid salt residue. Preferably throughout the process the maximum temperature of the hydrate inhibitor is kept below the degeneration temperature of the hydrate inhibitor.

In one embodiment of the present invention hydrate inhibitor is MEG and the maximum temperature is kept below 200-220° C., preferably below 180-200° C.

In another aspect of the present invention the moisture content of the dry solid salt residue is less than 2 w/w-% preferably less than 1 w/w %.

In another embodiment of the invention the method is performed continuously.

BRIEF DESCRIPTION OF THE DRAWINGS

The present invention will be described in further detail with reference to the enclosed figures where.

PRINCIPAL DESCRIPTION OF THE INVENTION

The present invention is directed towards a system and method for recovering inhibitor from the separated streams containing solid particles including solid salts mixed with inhibitor, water and dissolved salts. Such streams are in a traditional recovery plant obtained both initially after a pretreatment and after a reclamation process. The stream separated after pretreatment normally contains solid earth alkali salts such as $CaCO_3$ and other secondary salts such as $FeCO_3$ in a mixture of water and inhibitor containing a variety of dissolved salts. The stream obtained from the reclamation will contain solid alkali salts such as NaCl, KCl etc. and the liquid phase will generally have a higher inhibitor ratio than the liquid phase of the stream obtained from the pretreatment.

One of the commonly used hydrate inhibitors is monoethylene-glycol (MEG). MEG as well as other known inhibitors is sensitive to degeneration and higher temperatures and therefore the temperature through out the whole process should be kept below the degeneration temperature. For MEG the maximum temperature should be below 200-220° C. preferably below 180-200° C.

Figure 1:
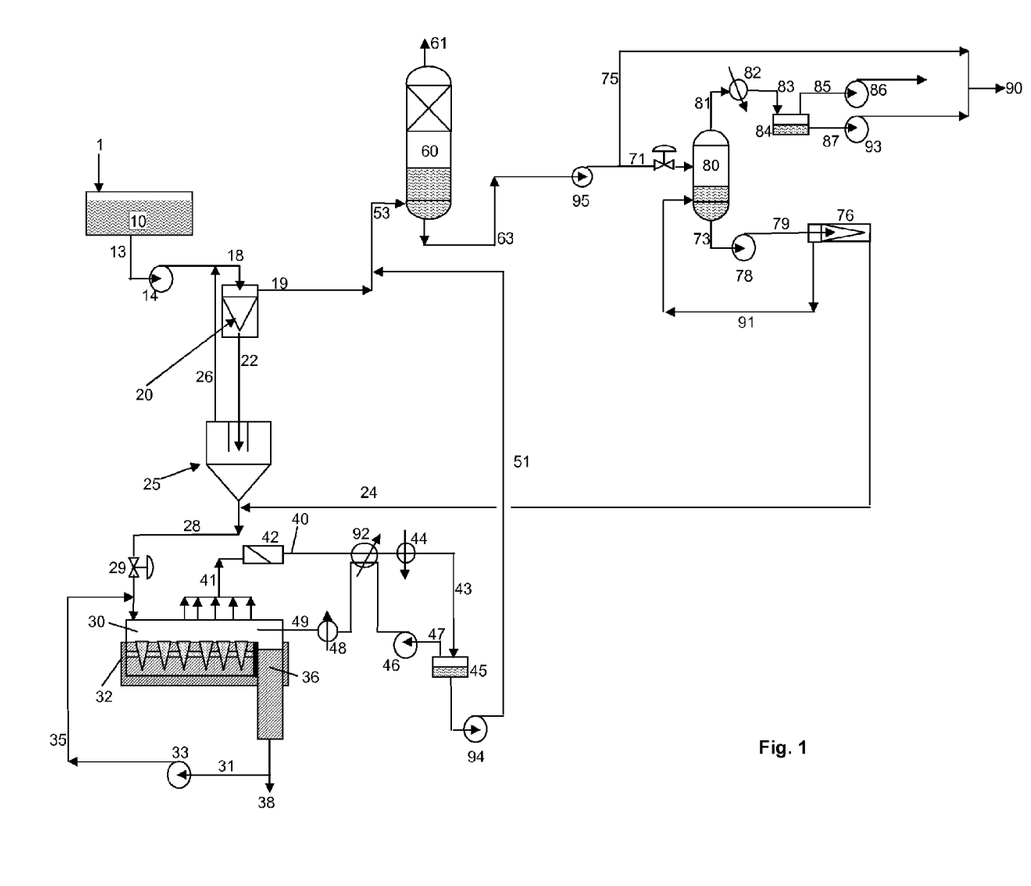
FIG. 1 illustrates an example of a hydrate inhibitor recovery process including one embodiment of the present invention.

The present invention will now be discussed in further detail with reference to the enclosed figures. The figures are schematic illustrations of embodiments of systems and methods according to the present invention. A person skilled in the art will understand that details such as valves, supply of heating and cooling media etc. are omitted to better illustrate the main principals of the present invention. FIG. 1 shows a full hydrate inhibitor recovery process including one embodiment of the present invention. The figure illustrates one of many possible processes and it will be appreciated that the present invention is equally applicable for recovering hydrate inhibitor from other processes resulting in rest streams comprising solid salts, water, hydrate inhibitor and dissolved salts.

In FIG. 1 the recovery process is illustrated as a three step process, pre-treatment, reconcentration and reclamation. A mixture of water, hydrate inhibitor and salts are obtain by phase separation of the well bore stream and enters the system as stream 1, also called rich MEG which is passed to a holding vessel 10 where the alkalinity and pH is controlled and the rich MEG is heated (not shown) and held, or circulated, to obtain forced precipitation of divalent cations in the rich MEG.

A stream 13 from the holding vessel 10 is passed via pump 14 as stream 18 into a solid separation unit 20. The unit is illustrated as a disk stack type centrifuge but other methods for solid separation are equally applicable. The disc stack type centrifuge can handle the full process flow, but the stream 22 comprising the solid salt particles has relatively high moisture content. The remaining liquid containing dissolved salts is transported as stream 19 to the second recovery process.

The stream enters the main reconcentration unit 60 as stream 53, wherein water is evaporated by heating (not shown) and leaves over the top as stream 61. The liquid stream 63 leaving the main reconcentration unit 60 has a high concentration of hydrate inhibitor and the main part thereof is transported via line 75 to the lean hydrate inhibitor stream 90 applicable for reuse. However to limit the salt concentration a slip stream 71 is removed for further processing. The slip stream is fed to a column 80 and the hydrate inhibitor is evaporated by heating (not shown) under vacuum provided by vacuum pump 86 connected to the top over line 85. The vapour stream 81 is cooled in heat exchanger 82 which results in condensation of the evaporated hydrate inhibitor. Via line 83 the top stream is fed to a separator 84. The condensed salt free hydrate inhibitor slip stream is supplied to the lean hydrate inhibitor stream 90 by pump 93 via line 87.

A bottom stream 73 is via pump 78 fed as stream 79 to a centrifuge unit 76, preferably a decanter type centrifuge, to obtain a stream 24 comprising salt particles and a liquid stream 91 which is recycled to the column 80. The stream 24 comprising salt particles from the reclamation process is together with the stream 22 comprising solid salt particles from the pretreatment process fed to a hydrate inhibitor recovery process according to the present invention.

In the illustrated embodiment the stream 22 is passed through a further gravity based thickening unit 25 and any separated liquid is returned upstream the centrifuge 20, however the utilisation of the gravity based thickening unit 25 is optional.

The slurry comprising salt particles is fed via line 28 through valve 29 and into a paddle dryer 30. The paddle dryer 30 is heated by a heating jacket 32 and optionally by heated paddles. The heating results in the evaporation of water and hydrate inhibitor and over time in the formation of dry salt particles. The rotation of the paddles enhances the heat transfer to the slurry. The whole paddle dryer has an angle compared to the horizontal plane, so that the salt by gravitation flows from the entry side to a salt over flow 36. The dry salt leaves the process through outlet 38. In the illustrated embodiment a smaller stream 31 of dry salt particles are via pump 33 and line 35 returned to the inlet. The pump 33 could be any displacement equipment suitable to transport salt, such as screw pump, blower or conveyor belt etc. This return line 35 makes it possible to regulate the humidity of the feed to the paddle dryer. This can be employed to avoid conditions where slurry permanently sticks to the inner surfaces of the salt paddle dryer and reduces the overall heat transfer, or to avoid liquid flow over the overflow gate in the paddle dryer. The stickiness of the feed varies with the salt composition (types of salt, salt particle sizes, particle distributions), chemicals used in the process and the humidity. Hence the stickiness can fluctuate under operation as reservoir salt composition may change over production time. So the control of the humidity of the feed by controlled return of dry salt through line 35 can bring additional flexibility and increased efficiency to the system. This is however an optional embodiment, as no dry salt need to be returned if there are non stickiness problem.

Evaporated hydrate inhibitor and water is withdrawn through one or several outlets in the top of the salt paddle dryer all connected to line 41 and optionally passed through a filter 42 before entering a cooler 44 for condensation of the vapour, obtaining cooled stream 43. The condensed hydrate inhibitor can be returned anywhere in the system. Optionally the stream 41 containing inhibitor and water vapour can be directly returned to the reclamation process upstream the centrifuge 20 as it still might contain some carried over dried particles. The stream 40 downstream filter 42 can be directly returned anywhere in the system.

Figure 7:
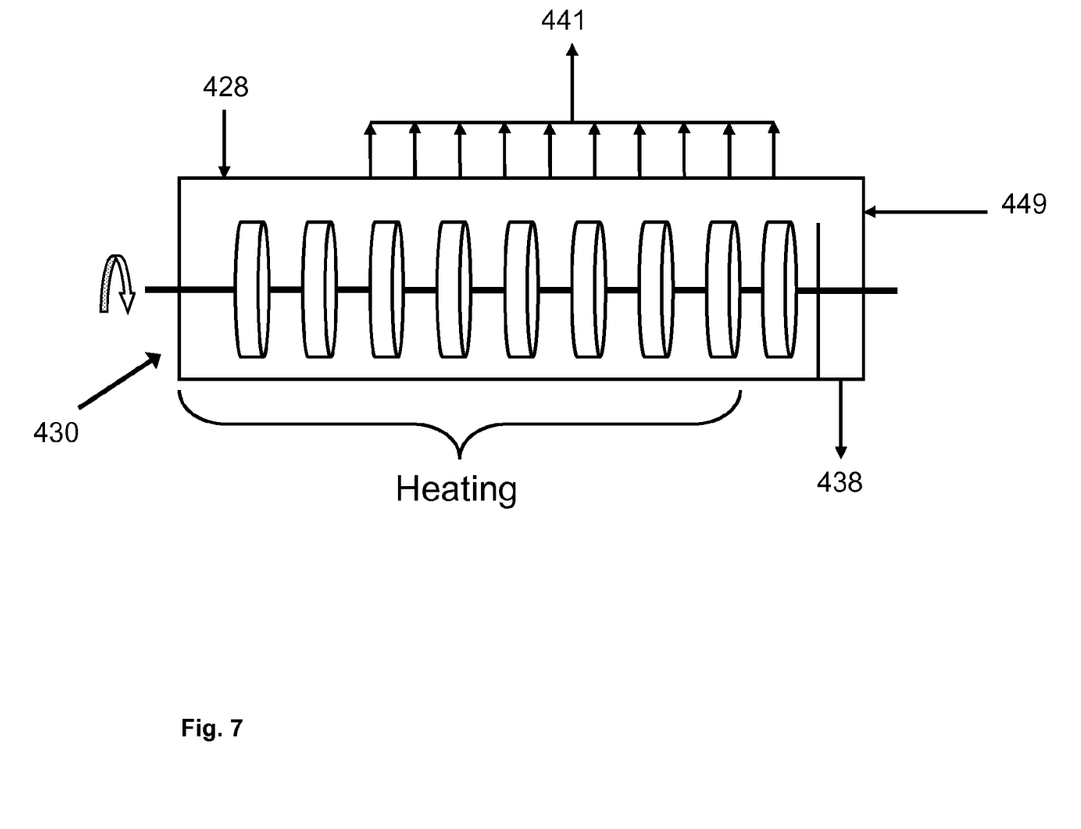
FIG. 7 illustrates a third embodiment of a paddle dryer.

In the illustrated embodiment however an inert sweep gas stream is employed to improve the transport of evaporated hydrate inhibitor out of the paddle dryer unit 30. The cooled stream 43 is therefore transported to a separator unit 45 where the condensed liquid comprising hydrate inhibitor and water is separated from the inert gas and via pump 94 in line 51 introduced to the fed line to the reconcentration unit 60. The inert gas is recycled as sweep gas via stream 47, pump 46, and heater 48 and reintroduced to the paddle dryer through line 49. For energy recovery purposes optionally a cross heat exchanger 92 may be employed between the inert sweep gas flow entering 48 and the stream 40 exiting the paddle dryer 30. Such cross heat exchanger 92 is beneficial when the paddle dryer cools the dried salts at the end, as illustrated in FIG. 7, since much larger volumes of sweep gas is required to avoid condensation of evaporated hydrate inhibitor in the paddle dryer.

In an alternative embodiment (not illustrated) the liquid stream 18 is passed directly to the gravity based thickening unit 25, without using a disc type centrifuge 20, where the clarified liquid is passed into main reclamation unit 60, and the thickened liquid is feed via line 28 through valve 29 and into a paddle dryer 30. The advantage of this configuration is that avoidance of the use a disc type centrifuge 20, but on the other hand one need to use a much larger based thickening unit 25.

Figure 2:
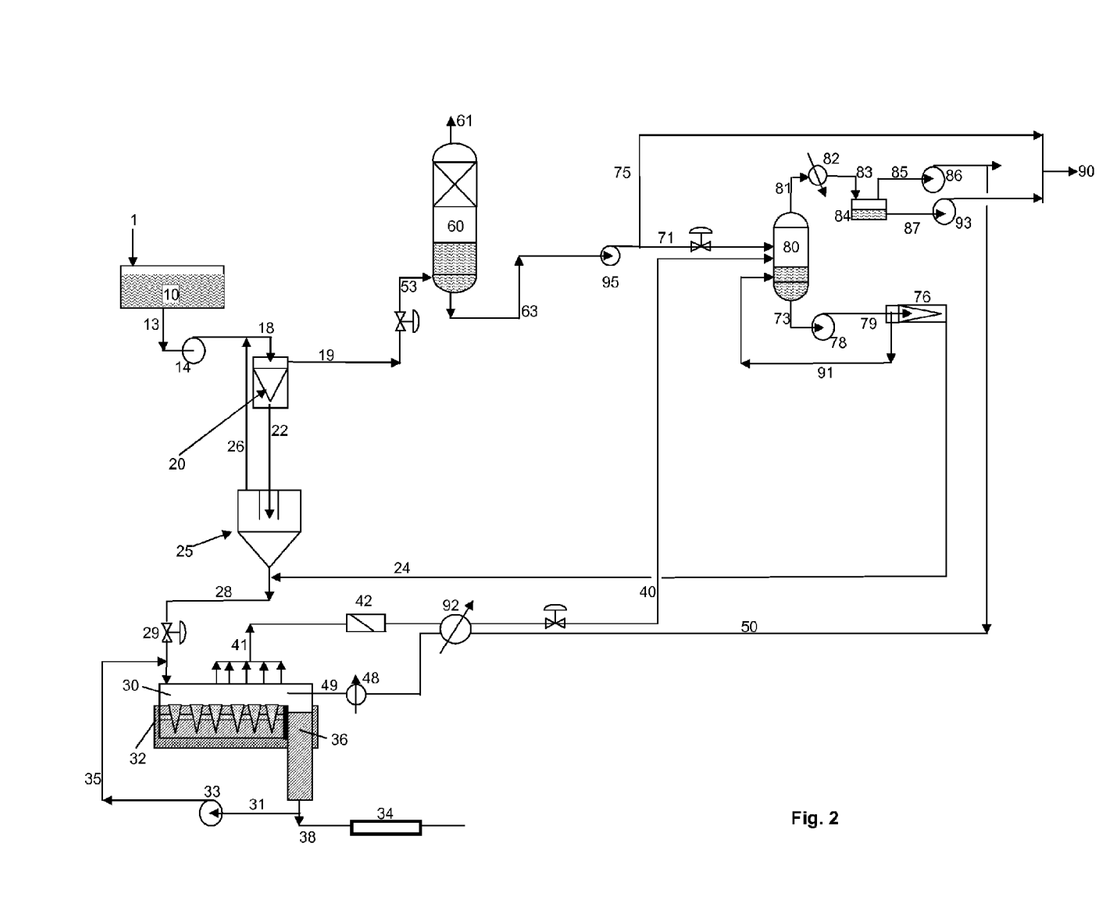
FIG. 2 schematically illustrates another hydrate inhibitor recovery process including an embodiment of the present invention.

FIG. 2 illustrates another embodiment of the present invention, wherein the gas stream 41 from the salt paddle dryer 30 after having passed the optional filter 42 is directly passed onto the column 80 as stream 40. The vacuum applied to column 80 by vacuum pump 86 accordingly drives the gas stream out of the paddle dryer. Inert sweep gas follows the top stream 81 out of the column 80 and continues through the system and into the vacuum pump 86. After having past the vacuum pump a stream 50 comprising mainly inert gas is returned via heater 48 as sweep gas to the paddle dryer. In this embodiment the vacuum system of the reclamation process is reused to drive the recirculation of sweep gas.

In the embodiment illustrated on FIG. 2 an optional separate salt cooler 34 is included as a separate unit in fluid communication with the dry salt outlet 38. An example of an applicable salt cooler is a screw conveyer with cooler or a paddle cooler. In the option using the cooler 34 the salt is not cooled within the salt paddle dryer and therefore the risk of recondensation of evaporated hydrate inhibitor and water on the salt within the paddle dryer is considerably limited. Due to this limited risk of recondensation the amount of sweep gas can be reduced resulting in increased efficiency, furthermore smaller size of salt paddle dryer will be required compared to when the salt paddle dryer need to comprise a cooling section.

Figure 3:
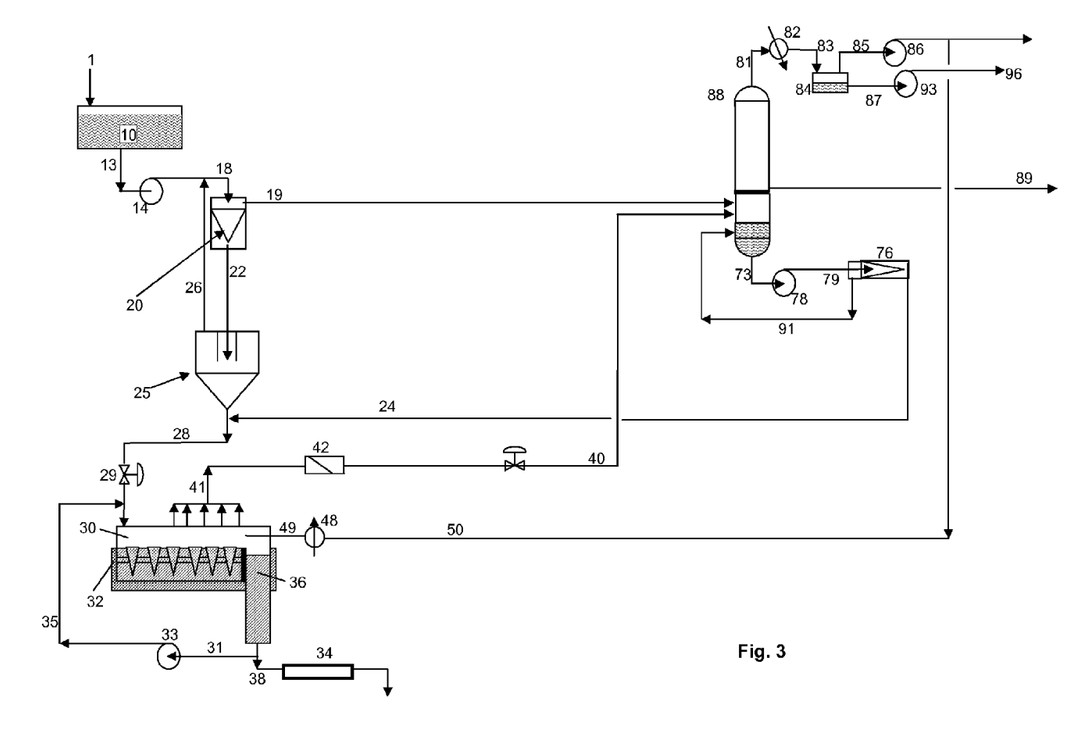
FIG. 3 schematically illustrates yet another hydrate inhibitor recovery process including an embodiment of the present invention.

FIG. 3 illustrates an embodiment of the present invention wherein the main unit of the reclamation is a flash separator unit 88 installed in exchange of column 80. This eliminates the need for the separate water removal section in FIG. 2 represented by column 60. In the embodiment of FIG. 3 the stream 19 is fed directly into the flash separation unit 88. The top stream 81 is generally handled in the same way as the top stream from column 80 and the vacuum pump 86 drives both the flash separator and the recirculation of sweep gas. However the liquid stream 96 from the separator 84 will consist of produced water and can be further treated as such. Lean hydrate inhibitor is obtained as stream 89 from a tray within the flash separator arranged above the inlet for stream 19.

Figure 4:
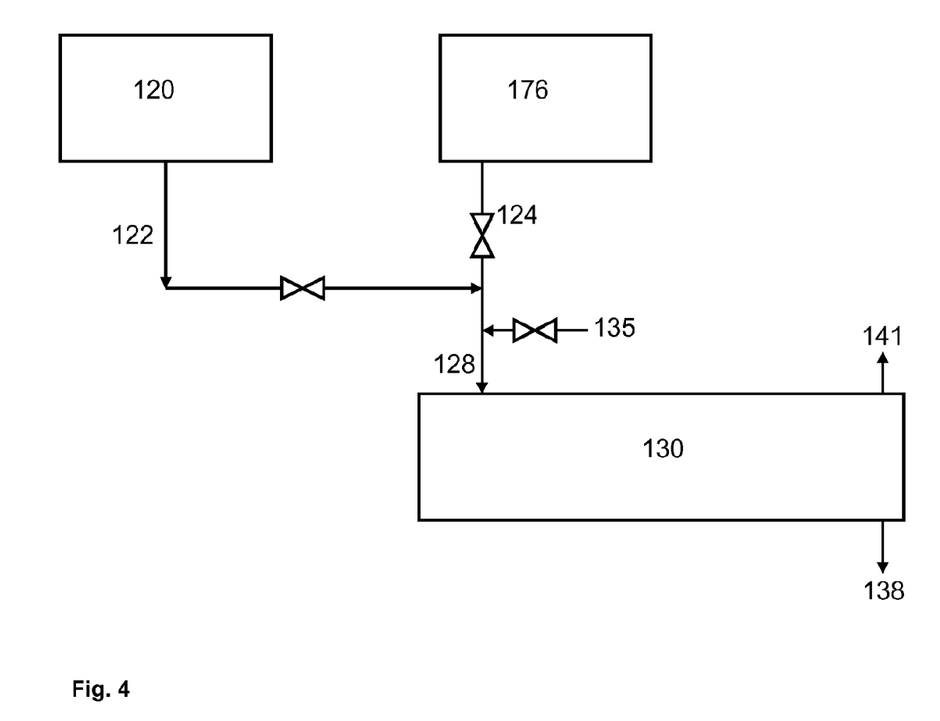
FIG. 4 schematically illustrates the principles of the present invention.
Figure 5:
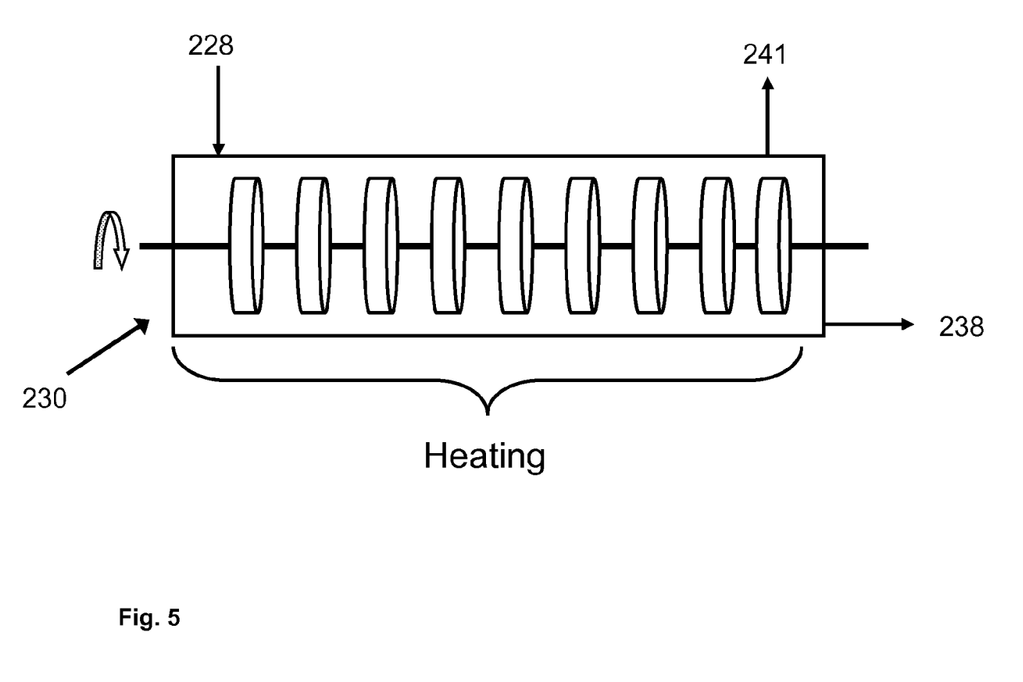
FIG. 5 illustrates one embodiment of a paddle dryer.

FIG. 4 illustrates a simplified schematic flow charge of a hydrate inhibitor recovery process. The pretreatment section 120 results in a first salt slurry stream 122 and the reclamation 176 results in a second salt slurry stream 124. The salt slurries are fed to a paddle dryer 130 resulting in a vapor phase 141 comprising water and hydrate inhibitor and a solid dry salt stream 138.

Optionally the composition of the slurries may be altered by an adjustment water stream 135. The adjustment stream may consist of dry salt as illustrated on FIG. 1, but it may however also be a water stream or both. The added water may be heated, but still by adding water as stream 135 additional heating energy may be required to evaporate the additional water. For slurry compositions with a low water to hydrate inhibitor ratio and a low liquid content, the adding of water results in an increased vapour flow where the water vapour acts as sweep stream. The adding of water to a salt slurry with a high hydrate inhibitor content, will reduce the evaporation temperature of the slurry. Hence the adding of water will lower the temperature required for the dryer, and thereby reducing the risk of degrading the hydrate inhibitor.

From different reservoirs the composition and amount of the different slurry streams will vary and also the selected technical solution for separating the slurry will alter the composition. However the present invention is not limited to a special slurry composition, and it should be appreciated that although the illustrated embodiment processes both salts streams as a mixture it is equally possible to treat each slurry stream separately or in parallel systems. It is an additional advantage of the present invention that the same system can be employed continuously to treat both salt slurry streams.

FIGS. 5 to 8 illustrates different embodiment of the paddle dryer and the present invention. On FIG. 5 the salt slurry 228 comprising water, hydrate inhibitor and salts enters the paddle dryer 230 at one end and leaves as vapour 241 and dry salt 238 respectively from the opposite end. Heating is provided throughout the whole paddle dryer.

Figure 6:
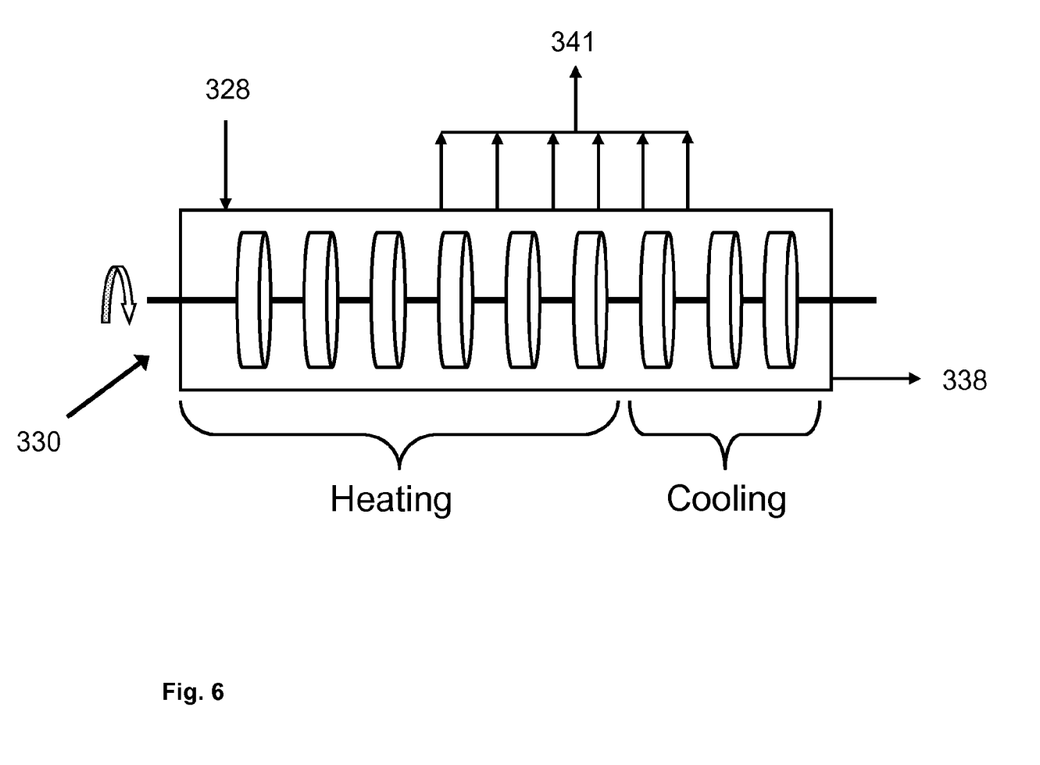
FIG. 6 illustrates a second embodiment of a paddle dryer.

In the embodiment illustrated on FIG. 6 the salt slurry 328 comprising water, hydrate inhibitor and salts enters the paddle dryer 330 at one end and leaves as vapour 341 and dry salt 338 respectively from the opposite end. However in this embodiment heating is not provided in the section of the paddle dryer 330 closest to the salt outlet 338. In stead cooling is provided so the dried powder can be safely handled as it exits the dryer. Typically this salt can be feed into so called big bags or containers. To limit condensation of evaporated water or hydrate inhibitor due to the cooled salt plural vapour outlets are arranged both in the heated and in the cooled section of the paddle dryer.

In the embodiment illustrated on FIG. 7 the salt slurry 428 comprising water, hydrate inhibitor and salts enters the paddle dryer 430 at one end and leaves as vapour 441 and dry salt 438 respectively from the opposite end. However in this embodiment no heating is provided in the last section of the paddle dryer closest to the dry salt outlet 438. Further to avoid condensation of vapour and increase the efficiency of the dryer an inert gas stream 449 is introduced as a counter current sweep stream. For effective removal of sweep gas and vapour a number of vapour outlets are arranged along the paddle dryer. The inert gas can be any available gas inert with respect to the compounds present. One example of an applicable gas is oxygen free nitrogen.

Figure 8:
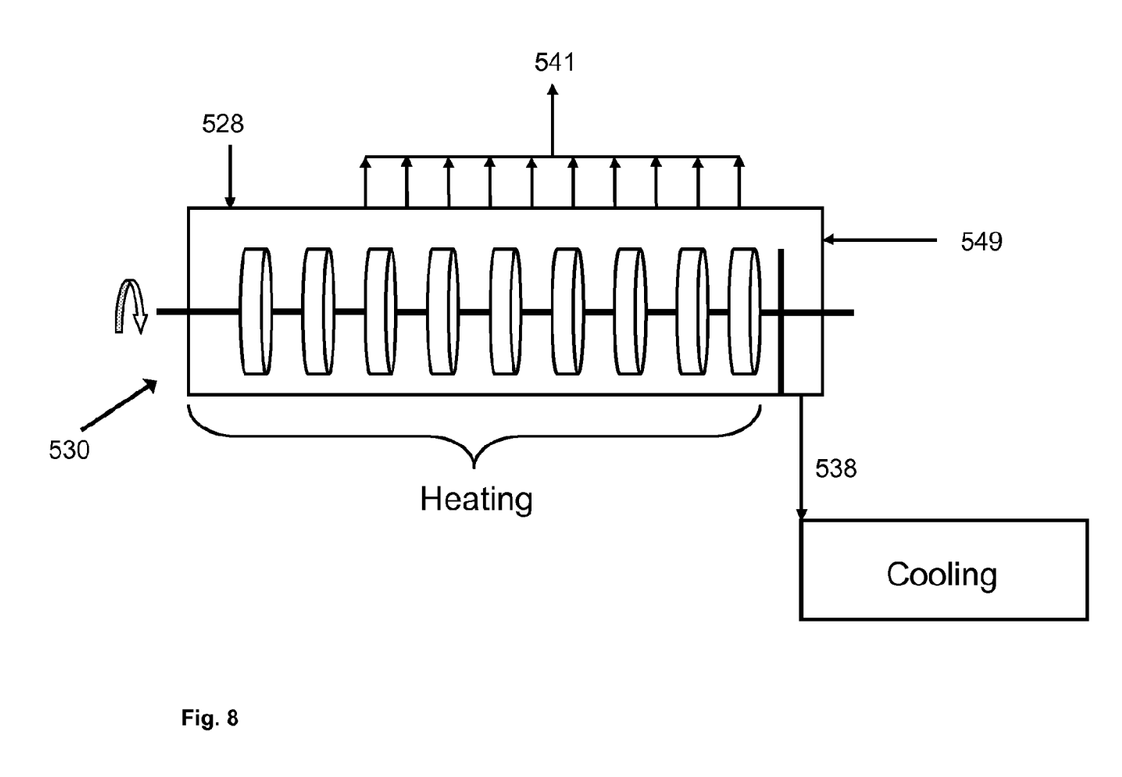
FIG. 8 illustrates a fourth embodiment of a paddle dryer.

In the embodiment illustrated on FIG. 8 the salt slurry 528 comprising water, hydrate inhibitor and salts enters the paddle dryer 530 at one end and leaves as vapour 541 and dry salt 538 respectively from the opposite end. However in this embodiment the dry salt stream 538 is past on to a separate cooling unit to regain heating energy. An inert gas stream 549 is introduced to assist the evaporation.

Although the embodiments illustrated on FIGS. 5-8 are presented as separated embodiment a person skilled in the art will appreciate the possibility of combining the different embodiments.

The invention claimed is:

1. A method for recovering a hydrate inhibitor from a fluid comprising water, the hydrate inhibitor, mineral salt ions and salt particles, wherein the hydrate inhibitor is mono-ethylene glycol (MEG) or glycol with other substituents, and the method comprises
   evaporating water and the hydrate inhibitor from the fluid with an indirectly heated paddle dryer, thereby obtaining vapor and a dry solid salt residue; and
   recovering the hydrate inhibitor from the vapor.

2. The method according to claim 1, wherein the method further comprises increasing a concentration of salt particles in the fluid by centrifugation prior to the evaporation, whereby a separate liquid stream is obtained.

3. The method according to claim 2, wherein the hydrate inhibitor is recovered from the separate liquid stream.

4. The method according to claim 2, wherein the method further comprises combining the separated liquid with the vapor to achieve a combined stream, and recovering the hydrate inhibitor from the combined stream.

5. The method according to claim 1, wherein the recovering is obtained by a combination of water separation, evaporation and condensation.

6. The method according to claim 1, wherein the method further comprises sweeping with an inert sweep gas stream over the fluid in the indirectly heated paddle dryer during the evaporation.

7. The method according to claim 6, wherein the inert sweep gas is separated from the vapor, heated and recycled as sweep gas.

8. The method according to claim 6, wherein the inert sweep gas stream before entering the paddle dryer is heat exchanged with the vapor.

9. The method according to claim 1, wherein the method further comprises cooling the dry solid salt residue.

10. The method according to claim 1, wherein a maximum temperature of the hydrate inhibitor is kept below a degeneration temperature of the hydrate inhibitor.

11. The method according to claim 10, wherein the hydrate inhibitor is MEG and the maximum temperature is kept below 220° C.

12. The method according to claim 1, wherein the method is performed continuously.

13. The method according to claim 11, wherein the maximum temperature is kept below 200° C.

14. The method according to claim 13, wherein the maximum temperature is kept below 180° C.

* * * * *